United States Patent

Lam et al.

[11] 4,045,557
[45] Aug. 30, 1977

[54] CERTAIN FORMAMIDINE DITHIOPHOSPHATES AND PHOSPHONATES AND THEIR USE AS INSECTICIDES

[75] Inventors: Hsiao-ling Lam; Eugene G. Teach, both of El Cerrito, Calif.

[73] Assignee: Stauffer Chemical Company, Westport, Conn.

[21] Appl. No.: 657,438

[22] Filed: Feb. 12, 1976

[51] Int. Cl.² .................. A01N 9/36; C07D 211/06
[52] U.S. Cl. .................. 424/200; 260/239 A; 260/239 B; 260/239 EP; 260/293.85; 260/326.42; 260/941; 424/211; 544/157
[58] Field of Search .................. 424/200; 260/293.85, 260/239 A, 239 EP, 239 B, 326.42

[56] References Cited

U.S. PATENT DOCUMENTS

| | | | |
|---|---|---|---|
| 3,806,560 | 4/1974 | Kishino et al. | 260/943 |
| 3,833,600 | 9/1974 | Toepfl | 260/293.85 |
| 3,948,940 | 4/1976 | Drabek | 260/326 E |
| 3,966,921 | 6/1976 | Beriger et al. | 424/200 X |

Primary Examiner—Leonard Schenkman
Attorney, Agent, or Firm—Joel G. Ackerman

[57] ABSTRACT

Compounds having the formula

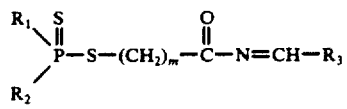

in which $R_1$ is lower alkyl or lower alkoxy, $R_2$ is lower alkoxy or methylthio-substituted lower alkoxy, and $R_3$ is

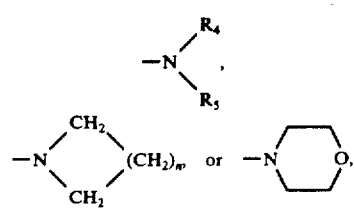

$R_4$ and $R_5$ are lower alkyl, $m$ is 1 or 2 and $n$ is 0 or an integer from 1 to 4. The compounds have utility as insecticides and acaricides.

43 Claims, No Drawings

CERTAIN FORMAMIDINE DITHIOPHOSPHATES AND PHOSPHONATES AND THEIR USE AS INSECTICIDES

DESCRIPTION OF THE INVENTION

This invention relates to certain novel formamidine dithiophosphates and -phosphonates. More particularly, this invention relates to certain novel formamidine dithiophosphates and -phosphonates having the formula

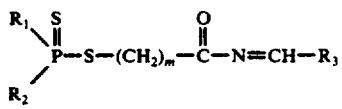

in which $R_1$ is lower alkyl or lower alkoxy, $R_2$ is lower alkoxy or methylthio-substituted lower alkoxy, $R_3$ is

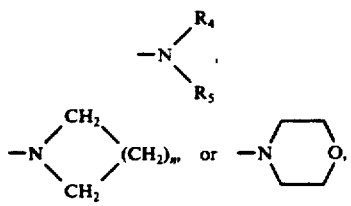

$R_4$ and $R_5$ are lower alkyl, m is 1 or 2, and n is 0 or an integer from 1 to 4.

By the terms "lower alkyl" and "lower alkoxy" are meant such groups containing from 1 to about 6 carbon atoms, preferably from 1 to about 4 carbon atoms, for instance, methyl, ethyl, n-propyl, isopropyl, n-butyl, isobutyl, sec.-butyl, tert.-butyl, amyl, hexyl and the like, and methoxy, ethoxy, n-propoxy, isopropoxy, n-butoxy, isobutoxy, sec.-butoxy, and the like.

In one embodiment, $R_1$ is lower alkyl while $R_2$ is lower alkoxy; the compounds are phosphonates.

In another embodiment, both $R_1$ and $R_2$ are lower alkoxy; the compounds are phosphates.

When $R_3$ is

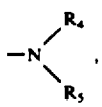

$R_4$ and $R_5$ may be the same or different lower alkyl moieties.

In another aspect, the invention also relates to a process or method for controlling insects by applying to the insect or the habitat thereof an insecticidally effective amount of a compound having the formula

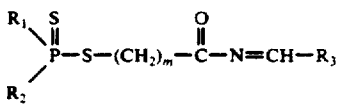

in which $R_1$ is lower alkyl or lower alkoxy, $R_2$ is lower alkoxy or methylthio-substituted lower alkoxy, $R_3$ is

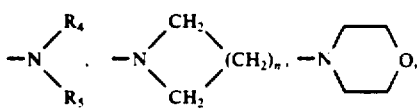

$R_4$ and $R_5$ are lower alkyl, m is 1 or 2 and n is 0 or an integer from 1 to 4.

Various methods of controlling insects involve the use of the various embodiments of the compounds of the present invention mentioned above.

The compounds of the present invention are prepared in general by the following method:

The novel compounds of this invention may be prepared by a three-step process. In the first step, an amine having the formula $R_3$H is reacted with an acetal of a formamide, for instance, N, N-dimethylformamide dimethyl acetal, to form the corresponding N-formyl acetal:

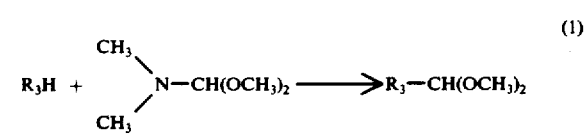

(1)

In the second step, the N-formyl acetal is reacted with a chloroalkylamide to produce a formamidine:

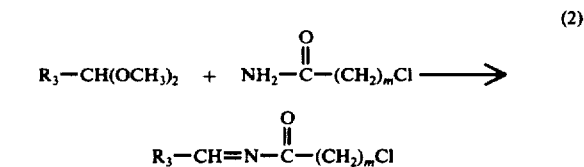

(2)

Finally, the formamidine is reacted with a dithiophosphate or -phosphonate to produce the desired compound:

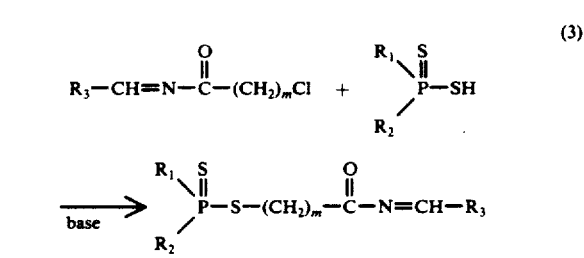

(3)

The following examples demonstrate the preparation of two compounds of the present invention a. 85 g (1 mole) of piperidine and 119 g (1 mole) of N,N-dimethylformamide dimethyl acetal were mixed and warmed slowly with stirring. After 3 hours, the reaction product was fractionally distilled. There was obtained 76.8 g (0.48 mole, 48% of theoretical yield) N-formylpiperidine dimethyl acetal.

b. 48 g (0.3 mole) of acetal produced in step (a) was mixed with 0.3 mole 2-chloroacetamide and 200 ml benzene and the mixture warmed to about 35° C with stirring for ½ hour. The benzene was removed under mild vacuum at about 30° C. for 1 hour. The product was stripped, yielding 60 g (0.39 mole, 106% of theoretical yield) of N-chloroacetylformimino-piperidine, as a semi-solid product.

c. To 23.8 g (0.14 mole) 0-ethyl, ethyldithiophosphonic acid in 120 ml of benzene, being cooled in an ice bath, was added 14.14 g (0.14 mole) triethylamine in 50 ml benzene, followed by 26.4g(0.14 mole) of the N-chloroacetylformimino-piperidine from step (b), also in 50 ml benzene. The mixture was heated under reflux for 2 hours, and stripped. The product was dissolved in ether and water; the ether solution was washed with water, dried over MgSO₄, decolorized and stripped. There was obtained 34.5 g (0.107 mole, 73% of theoretical yield) (O-ethyl ethyl dithiophosphonylacetyl)formimino-piperidine (compound 9 of the following Table I), $n_D^{30}$ 1.5762.

d. 22.32 g (0.12 mole) O,O'-diethyl dithiophosphoric acid was mixed with 50 ml of a 25% solution of sodium methoxide in methanol (i.e., 0.12 mole sodium methoxide). The mixture was stirred and stripped, producing 24 g of a white powder, believed to be the sodium salt of the acid. The white powder was stirred in 120 ml acetone and 22.6 g (0.12 mole) N-chloroacetylformimino-piperidine, prepared in step (b), dissolved in 100ml acetone, was added. The mixture was refluxed for 2 hours and stripped. The residue was dissolved in ether and water, the ether solution washed with water, dried over MgSO₄, decolorized and stripped. There was obtained 31.5 g (0.093 mole, 77.6% of theoretical yield) (O,O' diethyldithiophosphoryl)formimino-piperidine (compound 10 of Table I), $n_D^{30}$ 1.5592.

The following table 1 lists representative compounds of the present invention which may be prepared according to the above procedures.

Table 1

$$R_1\underset{R_2}{\overset{S}{\underset{\|}{\diagdown}}}P-S-(CH_2)_m-\overset{O}{\underset{\|}{C}}-N=CH-R_3$$

| Compound | m | R₁ | R₂ | R₃ | $n_D^{30}$ |
|---|---|---|---|---|---|
| 1 | 1 | C₂H₅O | C₂H₅O | N(CH₃)₂ | 1.5521 |
| 2 | 1 | C₂H₅ | C₂H₅O | N(CH₃)₂ | 1.5628 |
| 3 | 1 | CH₃O | CH₃O | N(CH₃)₂ | 1.5302 |
| 4 | 1 | C₂H₅ | i-C₃H₇O | N(CH₃)₂ | 1.5573 |
| 5 | 1 | C₂H₅ | CH₃O | N(CH₃)₂ | 1.5770 |
| 6 | 1 | C₂H₅ | CH₃S(CH₂)₂O | N(CH₃)₂ | 1.6057 |
| 7 | 1 | C₂H₅ | s-C₄H₉O | N(CH₃)₂ | 1.5528 |
| 8 | 1 | C₂H₅ | CH₃O | piperidine | 1.5640 |
| 9 | 1 | C₂H₅ | C₂H₅O | piperidine | 1.5762 |
| 10 | 1 | C₂H₅O | C₂H₅O | piperidine | 1.5592 |
| 11 | 1 | C₂H₅ | i-C₃H₇O | piperidine | 1.5478 |
| 12 | 1 | C₂H₅ | s-C₄H₉O | piperidine | 1.5500 |
| 13 | 1 | C₂H₅ | C₂H₅O | morpholine | 1.5656 |
| 14 | 1 | C₂H₅O | C₂H₅O | morpholine | 1.5459 |
| 15 | 1 | C₂H₅ | CH₃O | morpholine | 1.5811 |
| 16 | 1 | C₂H₅ | C₂H₅O | N(C₂H₅)₂ | 1.5821 |
| 17 | 1 | C₂H₅O | C₂H₅O | N(C₂H₅)₂ | 1.4969 |
| 18 | 2 | C₂H₅ | C₂H₅O | N(CH₃)₂ | 1.5580 |

Insecticidal Evaluation Tests

The following insect species were used in evaluation tests for insecticidal activity.

1. Housefly (HF) — *Musca domestica* (Linn.)
2. German Roach (GR) — *Blatella germanica* (Linn.)
3. Lygus Bug (LB) — *Lygus hesperus* (Knight)
4. Bean Aphid (BA) — *Aphis fabae* (Scop.)
5. Green Peach Aphid (GPA) — *Myzus persicae* (Sulzer)
6. Salt Marsh Caterpillar (SMC) — *Estigmene acrea* (Drury)
7. Cabbage Looper (CL) — *Trichoplusia ni* (Hubner)
8. Tobacco Bud Worm (TBW) — *Heliothis virescens* (F.)
9. Southern House Mosquito (MOS) — *Culex pipiens quinquefasciatus* (Say)

The insecticidal evaluation tests were conducted as follows:

Housefly: Test compounds were diluted in acetone and aliquots pipetted onto the bottom of 55 × 15 mm aluminum dishes. To insure even spreading of the chemical on the bottom of the dishes, 1 ml of acetone containing 0.02% peanut oil was also added to each dish. After all solvents had evaporated, the dishes were placed in circular cardboard cages containing 25 female houseflies, 1 to 2 days old. The cages were covered on the bottom with cellophane and on top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The LD-50 values are expressed below in Table II under the heading HF, in terms of μg of the test compound per 25 female flies.

German Cockroach: Test compounds were diluted in a 50-50 acetone-water solution. 2 cc of the solution were sprayed through a DeVilbiss type EGA hand spray gun into circular cardboard cages containing 10 one-month-old German cockroach nymphs. The test cages were covered on the bottom with cellophane and on the top with tulle netting. Percent mortality was recorded 7 days later. Test concentrations ranged from 0.1% down to that at which approximately 50% mortality occurred. LD-50 values are expressed below in Table II under the heading GR in terms of percent of the test compound in the sprayed solution.

Lygus Bug: Test compounds were diluted in a 50-50 acetone-water solution. 2 cc of the solution were sprayed through a DeVilbiss type EGA hand spray gun into circular cardboard cages containing 1 string bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. LD-50 values are expressed below in Table II under the heading LB in terms of percent of the test compound in the sprayed solution.

Black Bean Aphid: Nasturtium plants (*Tropaeolum* sp.), approximately 5 cm tall, were transplanted into sandy loam soil in 3-inch clay pots and infested with 25–50 black bean aphids of mixed ages. 24 hours later they were sprayed to the point of runoff with 50-50 acetone-water solutions of the test chemicals. Treated plants were held in the greenhouse and mortality was recorded after 7 days. Test concentrations ranged from 0.05% down to that at which 50% mortality occurred. LD-50 values are expressed below in Table II under the heading BA in terms of percent of the test compound in the sprayed solution.

Green Peach Aphid: Radish plants (*Rhaphanus sativus*), approximately 2 cm tall, were transplanted into sandy loam soil in 3-inch clay pots and infested with 25-50 green peach aphids of mixed ages. 24 hours later they were sprayed to the point of runoff with 50-50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading GPA in terms of percent of the test compound in the sprayed solution.

Salt-Marsh Caterpillar: Test compounds were diluted in a 50-50 acetone-water solution. Sections of curly dock (*Rumex crispus*) leaves, approximately 1 × 1.5 inches, were immersed in the test solution for 2-3 seconds and placed on a wire screen to dry. The dried leaves were placed in petri dishes containing a moistened piece of filter paper and infested with 5 second-instar salt-marsh caterpillar larvae. Mortality of the larvae was recorded 48 hours later, and a piece of synthetic media was added to dishes containing survivors. These were then held for 5 additional days to observe for any delayed effects of the test chemicals.

Test concentrations ranged from 0.05% down to that at which approximately 50% mortality occurred. LD-50 values are expressed below in Table II under the heading SMC in terms of percent of the test compound in the solution.

Cabbage Looper: Test compounds were diluted in a 50-50 acetone-water solution. Cotyledons of hyzini squash (*Calabacita abobrinha*), approximately 1 × 1.5 inches, were immersed in the test solutions for 2-3 seconds and placed on a wire screen to dry. The dried leaves were placed in petri dishes containing a moistened piece of filter paper and infested with five second-instar cabbage looper larvae. Mortality of the larvae was recorded 48 hours later, and a piece of synthetic media added to dishes containing survivors. These were then held for 5 additional days to observe for any delayed effects of the test chemicals.

Test concentrations ranged from 0.1% to that at which approximately 50% mortality occurred. LD-50 values are expressed below in Table II under the heading CL in terms of percent of the test compound in the solution.

Tobacco Budworm: Test compounds were diluted in a 50-50 acetone-water solution. Sections of Romaine lettuce (*Latuca sativa*) leaves, approximately 1 × 1.5 inches, were immersed in the test solution for 2-3 seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe for any delayed effects of the test chemicals.

Test concentrations ranged from 0.1% to that at which approximately 50% mortality occurred. LD-50 values are expressed below in Table II under the heading TBW in terms of percent of the test compound in the solution.

Southern House Mosquito Larvae (*Culex pipiens quinquefasciatus* Say): Insecticidal activity was determined using third instar larvae of the mosquito *Culex pipiens quinquefasciatus*. Ten larvae were placed in a six ounce paper cup containing 100 ml. of an aqueous solution of the test chemical. The treated larvae were stored at 70° F, and 48 hours later the mortality was recorded. Test concentrations ranged from 0.5 down to that at which approximately 50% mortality occurred. LD-50 values are expressed below in Table II under the heading MOS in terms of ppm of the test compound in the solution.

Acaricidal Evaluation Test

The two-spotted mite (2SM), *Tetranychus urticae* (Koch), was employed in tests for miticides. The test procedure was as follows:

Pinto bean plants (Phaseolus sp.) approximately 10 cm tall, were transplanted into sandy loam soil in 3-inch clay pots and thoroughly infested wth two-spotted mites of mixed ages and sexes. 24 hours later, the infested plants were inverted and dipped for 2-3 seconds in 50-50 acetone-water solutions of the test chemicals. Treated plants were held in the greenhouse, and 7 days later mortality was determined for both the adult mites and the nymphs hatching from eggs which were on the plants at the time of treatment. Test concentrations ranged from 0.05% down to that at which 50% mortality occurred. LD-50 values are expressed below in Table II under the headings 2SM-PE (i.e., post-embryonic) and 2SM-Eggs, in terms of percent concentration of the test compound in the solution.

Systemic Evaluation Test

This test evaluates the root absorption and upward translocation of the candidate systemic compound. The two-spotted mite (2SM) *Tetranychus urticae*, (Koch) and the Bean Aphid (BA) — *Aphis fabae* (Scop.) were employed in the test for systemic activity. Tests were conducted as follows:

Two-Spotted Mite: Test chemicals were dissolved in acetone and aliquots diluted in 200 cc of water in glass bottles. Two pinto bean plants (Phaseolus sp.), with expanded primary leaves, were supported in each bottle by cotton plugs, so that their roots and stems were immersed in the treated water. The plants were then infested with 75-100 two-spotted mites of various ages and sexes. One week later the mortality of the adult mites and nymphs was recorded. Test concentrations in the medium ranged from 10 ppm down to that at which 50% mortality occurred.

Black Bean Aphid: Test chemicals were diluted in acetone and aliquots thoroughly mixed into 500 grams of dry, sandy loam soil. The treated soil was placed in a pint-sized carton and a nasturtium plant (Tropaeolum sp.) approximately 5 cm tall was transplanted into each carton. The plants were then infested with approximately 25 black bean aphids of mixed ages and placed in the greenhouse. 7 days later mortality was recorded. Test concentrations ranged from 10 ppm down to that at which approximately 50% mortality occurred.

LD-50 values are expressed below in Table II under the headings 2SM-S and BA(S) respectively, in terms of percent concentration of the test compound.

Table 2

| Compound No. | HF (μg) | GR (%) | LB (%) | BA (%) | BA(S) (ppm) | GPA (%) | SMC (%) | CL (%) | TBW (%) | MOS (ppm) | 2-SM PE (%) | 2-SM E (%) | (ppm) |
|---|---|---|---|---|---|---|---|---|---|---|---|---|---|
| 1 | 4 | .03 | >.05 | .0008 | 0.8 | .005 | >.05 | >0.1 | — | >1 | <.05 | <.05 | 3 |
| 2 | 0.3 | .003 | .003 | .0003 | 0.3 | .001 | >.05 | >0.1 | — | >1 | .005 | .005 | 0.5 |
| 3 | 80 | >0.1 | >.05 | >.05 | — | — | >.05 | >0.1 | — | >1 | <.05 | <.05 | >10 |
| 4 | 18 | .005 | .01 | .0003 | 0.3 | .001 | >.05 | — | — | 0.6 | .01 | .03 | 3 |
| 5 | 0.09 | .008 | .01 | .0008 | 3 | .001 | >.05 | .05 | .05 | 1 | <.05 | <.05 | 3 |
| 6 | >100 | >0.1 | .03 | .001 | 1 | .01 | >.05 | — | — | 0.2 | <.05 | <.05 | >10 |
| 7 | 30 | .01 | .03 | .0008 | 1 | .008 | >.05 | — | — | 0.6 | <.05 | <.05 | 5 |
| 8 | 0.8 | .01 | .005 | .001 | 1 | .008 | .05 | >0.1 | >0.1 | >1 | .01 | .03 | 0.5 |
| 9 | 1 | .008 | .0008 | .0008 | 0.3 | .001 | >.05 | >0.1 | 0.1 | >1 | .005 | .03 | 0.3 |
| 10 | 5 | .08 | .03 | .0008 | 1 | .01 | >.05 | >0.1 | >0.1 | >1 | <.05 | <.05 | 3 |
| 11 | 5 | .008 | .005 | .0001 | 0.1 | .003 | .05 | 0.1 | .08 | 1 | .003 | >.05 | 1 |
| 12 | 27 | .01 | .01 | .00008 | 0.3 | .01 | >.05 | 0.1 | .05 | 1 | <.05 | <.05 | 5 |
| 13 | 0.75 | .005 | .001 | .00005 | .03 | .003 | .05 | .08 | .05 | 0.8 | .003 | .03 | .03 |
| 14 | 9 | >0.1 | .05 | .003 | 3 | .05 | >.05 | — | — | >1 | .05 | <.05 | 5 |
| 15 | 3.3 | .005 | .002 | .003 | 10 | .002 | >.05 | .05 | .05 | >1 | .003 | .03 | 2 |
| 16 | 3.7 | .005 | .003 | .0001 | 1 | .002 | .05 | .03 | 0.1 | 1 | .002 | .03 | 0.8 |
| 17 | 20 | >0.1 | >.05 | .003 | 10 | .05 | >.05 | >0.1 | >0.1 | >1 | <.05 | <.05 | >10 |
| 18 | 40 | >0.1 | >.05 | .0003 | 5 | .005 | >.05 | >0.1 | >0.1 | >1 | .05 | <.05 | — |

The compounds of this invention are generally embodied into a form suitable for convenient application. For example the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite, diatomite; gypsum; clays, propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served in the compound is rendered active by external influences, such as light or by some physiological action which occurs when the compounds ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise between about 0.01 and about 80% by weight of the composition.

What is claimed is:

1. A compound having the formula

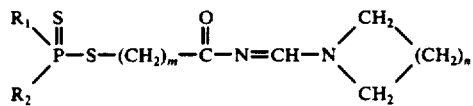

in which $R_1$ is lower alkyl or lower alkoxy, $R_2$ is lower alkoxy, or methylthio - substituted lower alkoxy, $m$ is 1 or 2 and $n$ is 0 or an integer from 1 to 4.

2. A compound according to claim 1 in which R is lower alkyl.

3. A compound according to claim 2 in which $R_1$ is ethyl.

4. A compound according to claim 1 in which $R_1$ is lower alkoxy.

5. A compound according to claim 4 in which $R_1$ is methoxy.

6. A compound according to claim 4 in which $R_1$ is ethoxy.

7. A compound according to claim 1 in which $R_2$ is lower alkoxy.

8. A compound according to claim 7 in which $R_2$ is methoxy.

9. A compound according to claim 7 in which $R_2$ is ethoxy.

10. A compound according to claim 7 in which $R_2$ is isopropoxy.

11. A compound according to claim 7 in which $R_2$ is sec.-butoxy.

12. A compound according to claim 1 in which $R_2$ is methylthioethoxy.

13. A compound according to claim 1 in which $R_1$ is lower alkyl and $R_2$ is lower alkoxy.

14. A compound according to claim 13 in which $R_1$ is ethyl and $R_2$ is ethoxy.

15. A compound according to claim 1 in which $R_1$ and $R_2$ are both lower alkoxy.

16. A compound according to claim 15 in which $R_1$ and $R_2$ are both ethoxy.

17. A compound according to claim 1 in which $n$ is 3.

18. A compound according to claim 1 in which $R_1$ is ethyl, $R_2$ is methoxy, $m$ is 1 and $n$ is 3.

19. A compound according to claim 1 in which $R_1$ is ethyl, $R_2$ is ethoxy, $m$ is 1 and $n$ is 3.

20. A compound according to claim 1 in which $R_1$ and $R_2$ are both ethoxy, $m$ is 1 and $n$ is 3.

21. A compound according to claim 1 in which $R_1$ is ethyl, $R_2$ is isopropoxy, $m$ is 1 and $n$ is 3.

22. A compound according to claim 1 in which $R_1$ is ethyl, $R_2$ is sec.-butoxy, $m$ is 1 and $n$ is 3.

23. A method for controlling insects comprising applying to the nsect or the habitat thereof an insecticidally effective amount of a compound having the formula

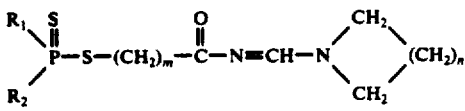

in which $R_1$ is lower alkyl or lower alkoxy, $R_2$ is lower alkoxy or methylthio-substituted lower alkoxy, $m$ is 1 or 2 and $n$ is 0 or any integer from 1 to 4.

24. A method according to claim 23 in which $R_1$ is lower alkyl.

25. A method according to claim 24 in which $R_1$ is ethyl.

26. A method according to claim 23 in which $R_1$ is lower alkoxy.

27. A method according to claim 26 in which $R_1$ is methoxy.

28. A method according to claim 26 in which $R_1$ is ethoxy.

29. A method according to claim 23 in which $R_2$ is lower alkoxy.

30. A method according to claim 29 in which $R_2$ is methoxy.

31. A method according to claim 29 in which $R_2$ is ethoxy.

32. A method according to claim 29 in which $R_2$ is isopropoxy.

33. A method according to claim 29 in which $R_2$ is sec.-butoxy.

34. A method according to claim 23 in which $R_2$ is methylthioethoxy.

35. A method according to claim 23 in which $R_1$ is lower alkyl and $R_2$ is lower alkoxy.

36. A method according to claim 35 in which $R_1$ is ethyl and $R_2$ is ethoxy.

37. A method according to claim 23 in which $R_1$ and $R_2$ are both lower alkoxy.

38. A method according to claim 37 in which $R_1$ and $R_2$ are both ethoxy.

39. A method according to claim 23 in which $n$ is 3.

40. A method according to claim 23 in which $R_1$ is ethyl, $R_2$ is ethoxy, $m$ is 1 and $n$ is 3.

41. A method according to claim 23 in which $R_1$ is ethyl, $R_2$ is isopropoxy, $m$ is 1, and $n$ is 3.

42. A method according to claim 23 in which $R_1$ is ethoxy, $R_2$ is ethoxy, $m$ is 1 and $n$ is 3.

43. An insecticidal composition comprising:
a. an insecticidally effective amount of a compound having the formula

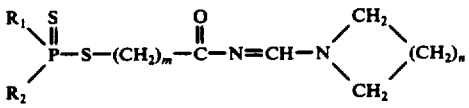

in which $R_1$ is lower alkyl or lower alkoxy, $R_2$ is lower alkoxy or methylthio-substituted lower alkoxy, $m$ is 1 or 2 and $n$ is 0 or an integer from 1 to 4, and (b) an inert carrier.